(12) United States Patent
Lee et al.

(10) Patent No.: US 11,219,698 B2
(45) Date of Patent: *Jan. 11, 2022

(54) METAL OXIDE NANOPARTICLE-BASED T1-T2 DUAL-MODE MAGNETIC RESONANCE IMAGING CONTRAST AGENT

(71) Applicant: INTRON BIOTECHNOLOGY, INC., Gyeonggi-do (KR)

(72) Inventors: Kwang Yeol Lee, Gyeonggi-do (KR); Min Sik Kim, Seoul (KR); Taek Hoon Kim, Seoul (KR); Ngoc Phan Vu, Hanoi (VN)

(73) Assignee: INTRON BIOTECHNOLOGY, INC., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/933,198

(22) Filed: Jul. 20, 2020

(65) Prior Publication Data

US 2021/0000983 A1    Jan. 7, 2021

Related U.S. Application Data

(62) Division of application No. 14/782,481, filed as application No. PCT/KR2013/002846 on Apr. 5, 2013, now abandoned.

(51) Int. Cl.
*A61K 49/18* (2006.01)
*C01G 45/02* (2006.01)
*B05D 7/00* (2006.01)

(52) U.S. Cl.
CPC ........ *A61K 49/186* (2013.01); *A61K 49/1818* (2013.01); *A61K 49/1875* (2013.01); *B05D 7/54* (2013.01); *C01G 45/02* (2013.01); *C01P 2002/72* (2013.01); *C01P 2004/04* (2013.01); *C01P 2004/38* (2013.01); *C01P 2004/84* (2013.01); *C01P 2004/90* (2013.01)

(58) Field of Classification Search
CPC .............. A61K 49/1818; A61K 49/186; A61K 49/1875; B05D 7/54; C01G 45/02; C01P 2002/72; C01P 2002/84; C01P 2002/04; C01P 2002/38; C01P 2002/90; C01P 2004/84; C01P 2004/04; C01P 2004/38; C01P 2004/90

See application file for complete search history.

(56) References Cited

U.S. PATENT DOCUMENTS

2011/0200534 A1    8/2011  Cheon et al.
2013/0195767 A1*   8/2013  Weissleder ............. A61K 49/10
                                                     424/9.323

FOREIGN PATENT DOCUMENTS

KR    20100111911 A    10/2010
WO    WO 2010/021519 A2    2/2010
WO    WO 2014/163222 A1    10/2014

OTHER PUBLICATIONS

Na, Appl. Phys. Lett., 2005, 87, p. 142504. (Year: 2005).*
Liu, J. Nanomaterials, 2013, p. 1-7. (Year: 2013).*
Eun Sook Choi et al. "Water-Soluble Ultra-Small Manganese Oxide Surface Doped Gadolinium Oxide ($Gd_2O_3$@Mno) Nanoparticles for MRI Contrast Agent", DOI: 10.1002/EJIC.201000374, Eur. J. Inorg. Chem. 2010, 4555-4560 © 2010 Wiley-VCH Verlag GmbH & Co. KGaA, Weinheim, XP-002763106.
Ki Hyun Bae et al. "Bioinspired Synthesis and Characterization of Gadolinium-Labeled Magnetite Nanoparticles for Dual Contrast $T_1$-and $T_2$-Weighted Magnetic Resonance Imaging" Department of Biological Sciences and Graduate School of Nanoscience and Technology, and Department of Electrical Engineering, Korea Advanced Institute of Science and Technology, Daejeon 305-701, South Korea. © 2010 American Chemical Society Published on Web Feb. 18, 2010.
Fengqin Hu et al., "Facile Synthesis of Ultrasmall PEGylated Iron Oxide Nanoparticles for Dual-Contrast $T_1$- and $T_2$-Weighted Magnetic Resonance Imaging", DOI10.1088/0957-4484/22/24/245604, © 2011 IOP Publishing Ltd.
Jongmin Shin et al., "Hollow Manganese Oxide Nanoparticles as Multifunctional Agents for Magnetic Resonance Imaging and Drg Delivery", XP-002762948 DOI: 10.1002/anie:200802323 © 2009 Wiley-VCH Verlag GmbH & Co. KGaA, Weinheim, Angew. Chem. Int. Ed. 2009, 48, 321-324.
Taekhoon Kim et al., "Urchin-Shaped Manganese Oxide Nanoparticles as pH-Responsive Activatable $T_1$ Contrast Agents for Magnetic Resonance Imaging", XP-002762949, DOI: 10.1002/anie. 201103108, Angew. Chem. Int. Ed. 2011, 50, 10589-10593, © 2011 Wiley-VCH Verlag GmbH & Co. KGaA, Weinheim.

(Continued)

*Primary Examiner* — Michael G. Hartley
*Assistant Examiner* — Leah H Schlientz
(74) *Attorney, Agent, or Firm* — von Briesen & Roper, s.c.

(57) ABSTRACT

The present invention relates to a magnetic resonance imaging (MRI) contrast agent, particularly a metal oxide nanoparticle-based T1-T2 dual-mode MRI contrast agent that can be used not only as a T1 MRI contrast agent but also as a T2 MRI contrast agent, and a method for producing the same. The metal oxide nanoparticle-based T1-T2 dual-mode MRI contrast agent can provide more accurate and detailed information associated with disease than single MRI contrast agent by the beneficial contrast effects in both T1 imaging with high tissue resolution and T2 imaging with high feasibility on detection of a lesion.

4 Claims, 15 Drawing Sheets

(56) References Cited

OTHER PUBLICATIONS

Geun Ho Im et al., "$Fe_3O_4$/Mno Hybrid Nanocrystals As A Dual Contrast Agent for Both $T_1$-and $T_2$-Weighted Liver MRI", XP-002763102, Biomaterials 34 (2013) 2069-2076.

Zijian Zhou et al., "A Synergistically Enhanced $T_1$-$T_2$ Dual-Modal Contrast Agent", XP-002763103, DOI: 10.1002/adma.201203169—Adv. Mater. 2012, 24, 6223-6228 © 2012 Wiley-VCH Verlag GmbH & Co. KGaA, Weinheim Dana E. Gheorghe et al., "Gold-Silver Alloy Nanoshells: A New Candidate for Nanotherapeutics and Diagnostics", XP-002763104.

* cited by examiner

METAL OXIDE NANOPARTICLE-BASED T1-T2 DUAL-MODE MAGNETIC RESONANCE IMAGING CONTRAST AGENT

CROSS-REFERENCE TO RELATED APPLICATION

This application is a divisional under 35 U.S.C § 121 of U.S. non-provisional patent application Ser. No. 14/782,481, filed on Oct. 5, 2015, which is a 35 USC § 371 U.S. national phase filing of International Patent Application No. PCT/KR2013/002846 filed on Apr. 5, 2013.

TECHNICAL FIELD

The present invention relates to a magnetic resonance imaging (MRI) contrast agent, particularly a metal oxide nanoparticle-based T1-T2 dual-mode MRI contrast agent that can be used not only as a T1 MRI contrast agent but also as a T2 MRI contrast agent.

BACKGROUND ART

Among various molecular imaging techniques, magnetic resonance imaging (MRI) is one of the most powerful and non-invasive diagnostic tools because MRI can provide image with excellent anatomical details based on the interaction of protons with the surrounding molecules of tissues.

MRI contrast agents are a group of contrast media used to improve the visibility of internal body structures by increasing contrast between normal tissues and abnormal tissues in MRI. MRI contrast agents alter the T1 (longitudinal) and T2 (transverse) relaxation times of tissues and body cavities where they are present. Depending on the image weighting, this can give a higher or lower signal. Most MRI contrast agents work through shortening the relaxation time of protons located nearby.

MRI contrast agent is defined by the two-principle nuclear magnetic resonance processes of spin relaxation, T1 (longitudinal), and T2 (transverse) (Journal of Nuclear Cardiology 11(6): 733-743, 2004).

Paramagnetic metal ions used as T1 MRI contrast agents principally accelerate T1 relaxation and produce the "bright" contrast in a T1-weighted image, whereas superparamagnetic metal oxides used as T2 MRI contrast agents primarily increase the rate of T2 relaxation and create "dark" contrast effects.

T1-T2 dual-mode MRI contrast agent can provide more accurate and detailed information associated with disease than single MRI contrast agent. The T1-T2 dual-mode strategy for MRI has attracted considerable interest because it can give highly accurate diagnostic information by the beneficial contrast effects in both T1 imaging with high tissue resolution and T2 imaging with high feasibility on detection of a lesion (Nat. Mater. 5: 971, 2006). Until now, T1-T2 dual-mode MRI contrast agent appropriate to clinical requirements has not been developed. Intensive attempts are required to develop T1-T2 dual-mode MRI contrast agents due to its prominent advantages for medical diagnosis.

Numbers of papers and patent descriptions have been cited in this description and the citation is marked in parentheses. The descriptions of cited papers and patent documents are attached in this invention so that the art and text of this invention can be more clearly understood.

DISCLOSURE

Technical Problem

It is an object of the present invention to overcome the problems of the prior art and thus to develop a technique and method long requested.

Precisely, it is an object of the present invention to provide a metal oxide nanoparticle-based T1-T2 dual-mode MRI contrast agent that can be used not only as a T1 MRI contrast agent but also as a T2 MRI contrast agent.

It is another object of the present invention to provide a method for producing a metal oxide nanoparticle-based T1-T2 dual-mode MRI contrast agent that can be used not only as a T1 MRI contrast agent but also as a T2 MRI contrast agent.

Technical Solution

To provide a metal oxide nanoparticle-based T1-T2 dual-mode MRI contrast agent, the present inventors developed a method to generate MRI contrast agents derived from nanoparticle with a core (T1 contrast material)-porous shell (T2 contrast material) structure by synthesizing metal oxide nanoparticles of T1 contrast material under inert gas environment, forming an epitaxial layer of metal oxide of T2 contrast material on the surface of metal oxide nanoparticles of T1 contrast material under inert gas environment, maintaining the formation of the layer of metal oxide of T2 contrast material under dry air environment to form multilayer nanoparticles having a core and porous shell structure, and coating multilayer nanoparticles with a biocompatible polymer, and then completed this invention by confirming that the nanoparticle-based MRI contrast agent could be used as T1-T2 dual-mode MRI contrast agent that can be used not only as a T1 MRI contrast agent but also as a T2 MRI contrast agent.

So, the present invention provides an MRI contrast agents derived from nanoparticle with a core (T1 contrast material)-porous shell (T2 contrast material) structure, and a method for producing the same. A sectional view illustrating one exemplary type of MRI contrast agent of the present invention is presented in FIG. 1.

In a preferred embodiment of the present invention, manganese oxide was selected as metal oxide of T1 contrast material, but not limited thereto and other metal oxides such as chromium (III) oxide and gadolinium (III) oxide can also be selected. Manganese oxide is more preferred. The present inventors were previously observed that manganese oxide was well functioned as a T1 contrast agent (Angew. Chem. Int. Ed. 50: 10589-10593, 2011).

In a preferred embodiment of the present invention, iron oxide is selected as metal oxide forming a porous shell structure, but not limited thereto and other superparamagnetic metal oxides can also be selected, which are exemplified by cobalt(II) oxide and nickel(II) oxide, but not limited thereto. Iron oxide is more preferred.

The image contrast enhancement of nanoparticle-based MRI contrast agents of the present invention is determined by the physical dimensions and morphology of the multilayer nanoparticle (i.e. high surface-to-volume ratio). For improvement of the image contrast enhancement, fine control of the physical dimensions and morphology of the multilayer nanoparticle is crucial. The present invention can provide a method to control these features of multilayer nanoparticles by controlling the physical dimensions and morphology of template cores (i.e., metal oxide nanoparticles of T1 contrast material) to give a high surface-to-volume ratio. These factors of template cores can be controlled by adjusting the amount of surfactant, reaction time, and reaction temperature. In addition, any shape of template cores can be selected for the present invention, which are exemplified by octahedral, cross-shaped, urchin-shaped, and cubic nanoparticles, but not limited thereto.

Various polymers can be used as a biocompatible polymer used in coating the multilayer nanoparticle with it. Preferred examples of the biocompatible polymers include biopolymers such as chitosan, elastin, hyaluronic acid, alginate, gelatin, collagen, and cellulose; and synthetic polymers such as polyethylene glycol (PEG), polyethylene oxide (PEO), polycaprolactone (PCL), polylactic acid (PLA), polyglycolic acid (PGA), poly(lactic-co-glycolic) acid (PLGA), poly (3-hydroxybutyrate-co-3-hydroxyvalerate) (PHBV), polydioxanone (PDO), poly(L-lactide-co-caprolactone), poly(ester urethane) (PEU), poly(L-lactide-co-D-lactide), poly (ethylene-co-vinyl alcohol), poly(acrylic acid) (PAA), poly(vinyl alcohol) (PVA), polyvinylpyrrolidone (PVP), polystyrene (PS) and polyaniline (PAN), but not limited thereto.

The said biocompatible polymers can be modified for improving biocompatibility and stability of MRI contrast agent. The methods useful for modification of polymer have been well-known and well-performed by those in the art, which means these methods are very general and thus no further explanation is necessary.

The said biocompatible polymers can be further modified by conjugation with various useful moieties such as targeting moieties or diagnostic moieties. The said targeting moieties include antibodies, antibody fragments, aptamers, and various ligands binding to receptors displayed on the surface of target cell, but not limited thereto. And the said diagnostic moieties include diagnostic imaging moieties such as fluorophores, optical reporters and quantum dots; computed tomography (CT) probes such as iodine-based compounds and gold nanoparticles; and nonmetallic radioisotopes such as indium (In), technetium (Tc) and fluorine (F), but not limited thereto. The methods for conjugation of polymers and useful moieties have been well-known and well-performed by those in the art, which means these methods are very general and thus no further explanation is necessary.

The MRI contrast agents of the present invention can be prepared by dispersion of the MRI contrast agent particles in pharmaceutically acceptable liquid media. The methods for preparation of pharmaceutically acceptable MRI contrast agent injectable composition have been well-known and well-performed by those in the art, which means these methods are very general and thus no further explanation is necessary.

The present invention also provides a method for producing a metal oxide nanoparticle-based T-T2 dual-mode MRI contrast agent that has a core of T1 contrast material and a porous shell of T2 contrast material formed on the core, which comprises the following steps:
  A) synthesizing metal oxide nanoparticles of T1 contrast material under inert gas environment
  B) forming an epitaxial layer of metal oxide of T2 contrast material on the surface of metal oxide nanoparticles of T1 contrast material under inert gas environment;
  C) maintaining the formation of the layer of metal oxide of T2 contrast material under dry air environment to form multilayer nanoparticles having a core and porous shell structure; and
  D) coating multilayer nanoparticles with a biocompatible polymer.

In a preferred embodiment of the present invention, thermal decomposition of metal precursors is utilized in synthesis of metal oxides of T1 and T2 contrast materials, but not limited thereto and other methods such as precipitation, gas evaporation method, mixed gas method, spray drying and mechanical alloying can also be used.

A variety of metal salts can be utilized as metal precursors, which are exemplified by metal acetate, metal acetylacetonate, metal bromide, metal carbonate, metal chloride, metal fluoride, metal iodide, metal nitrate, metal sulfate, metal oleate, metal formate, their hydrate forms, and mixture of the said metal salts, but not limited thereto.

As surfactants used in thermal decomposition of metal precursors, alkyl carboxylic acids such as oleic acid, lauric acid, stearic acid, mysteric acid and hexadecanoic acid; alkylamines such as oleylamine, laurylamine, hexadecylamine, trioctylamine and dioctylamine; and mixture of alkyl carboxylic acids or alkylamines can be used, but not limited thereto. As alkylamines, primary alkylamines such as oleylamine, laurylamine, hexadecylamine are more preferred.

As organic solvents used in thermal decomposition of metal precursors, organic solvents that have higher boiling point than the temperature of thermal decomposition reaction are preferred. Hydrocarbon compounds such as alkanes, alkenes, alkynes, cycloalkanes and alkadiens; ether compounds such as butyl ether, hexyl ether, octyl ether and decyl ether; heterocyclic compounds such as pyridine and tetrahydrofuran; aromatic compounds such as toluene, xylene, mesitylene and benzene; and amine compounds such as trioctylamine and oleylamine are exemplified, but not limited thereto.

The exposure of metal oxide nanoparticles of T1 contrast material to air during formation of a layer of metal oxide of T2 contrast material on the surface of metal oxide nanoparticles of T1 contrast material under dry air environment forms a thin layer of metal oxide with higher oxidation state. For example, in the presence of oxygen, the surface of MnO nanoparticles is partially converted to a $Mn_3O_4$ phase. This oxidation is not homogeneous, leading to formation of multiple domains of metal oxide with higher oxidation state on the surface of metal oxide nanoparticles of T1 contrast material. The presence of the patches of the higher oxidation state form of metal oxide of T1 contrast material on the surface of metal oxide nanoparticles of T1 contrast material is crucial to generate the porous metal oxide shell of T2 contrast material. Due to the existence of the pores in metal oxide shell of T2 contrast material, T1 contrast material can be easily functioned. In addition, the metal ion within the metal oxide with higher oxidation state diffuses out to the newly formed metal oxide shell of T2 contrast material during formation of an epitaxial layer of metal oxide of T2 contrast material on the surface of metal oxide nanoparticles of T1 contrast material. The higher oxidation state form of metal oxide of T1 contrast material is readily mixed with the newly formed metal oxide phase of T2 contrast material to form a T1 metal-doped metal oxide phase of T2 contrast material. As a result, nanoparticles that have a core of T1 contrast material and a shell of T1 metal-doped metal oxide of T2 contrast material can be synthesized. In some cases, this phenomenon can provide additional merits such as improvement of image contrast enhancement in T1- or T2-weighted image.

Consequently, performance of the reaction to generate the layer of metal oxide of T2 contrast material on the surface of metal oxide nanoparticles of T1 contrast material under dry air condition is very important.

Advantageous Effect

The present invention can provide a method for producing a metal oxide nanoparticle-based T1-T2 dual-mode MRI contrast agent that can be used not only as a T1 MRI contrast agent but also as a T2 MRI contrast agent. The MRI contrast agent made in accordance with the present invention can provide more accurate and detailed information associated with disease than single MRI contrast agent by the beneficial contrast effects in both T1 imaging with high tissue resolution and T2 imaging with high feasibility on detection of a lesion. According to the methods of the present invention, control of physical dimensions and morphology of the core and shell of nanoparticles can be possible; thus, increase the image contrast enhancement of both T1- and T2-weighted images can be anticipated.

DESCRIPTION OF DRAWINGS

The application of the preferred embodiments of the present invention is best understood with reference to the accompanying drawings, wherein.

MODE FOR INVENTION

As explained hereinbefore, the present invention is to provide a metal oxide nanoparticle-based T1-T2 dual-mode MRI contrast agent that can be used not only as a T1 MRI contrast agent but also as a T2 MRI contrast agent and a method for producing the same.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Figure 1:
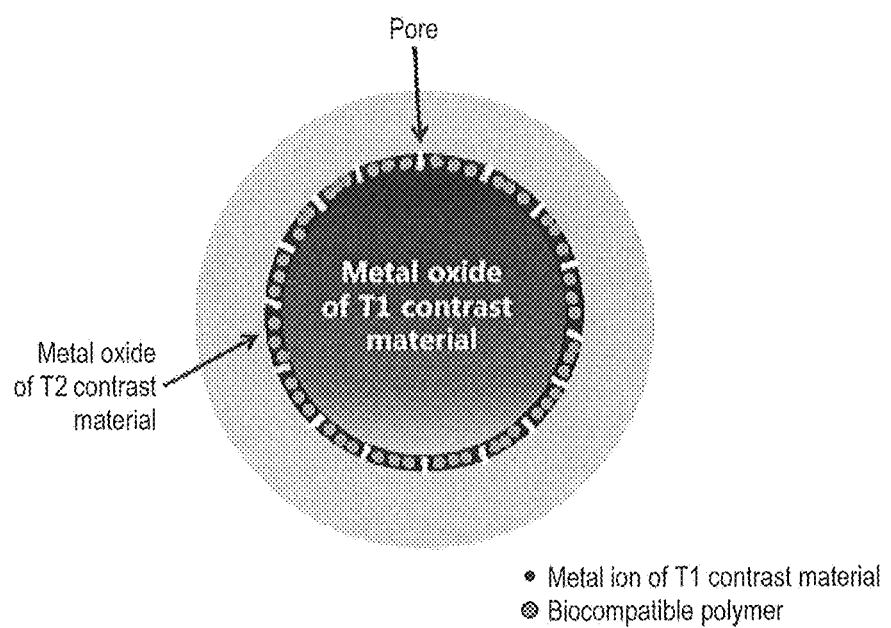
FIG. 1 is a sectional view illustrating one exemplary type of MRI contrast agent of the present invention.
Figure 2:
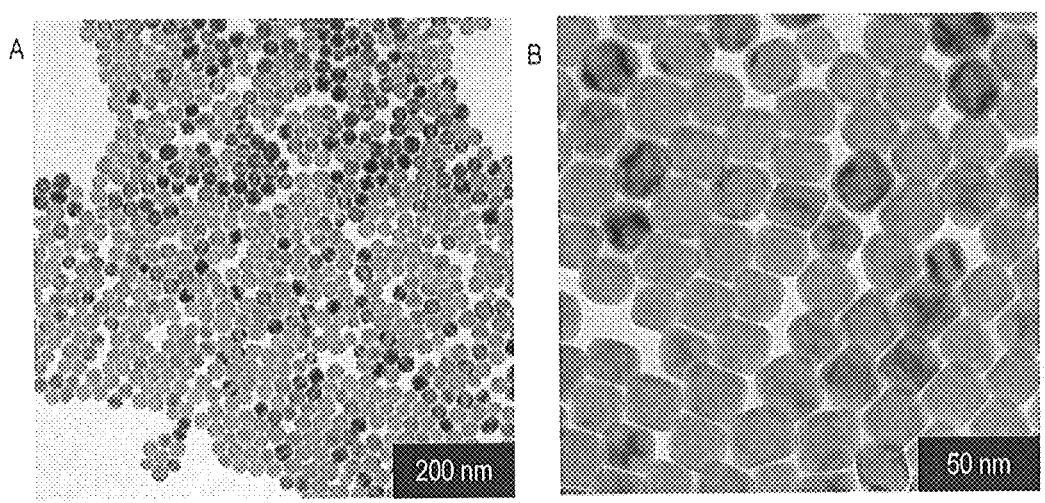
FIG. 2 is a transmission electron microscopy (TEM) image of octahedral manganese (II) oxide (MnO) nanoparticles. (a) Low magnification, and (b) high magnification.
Figure 3:
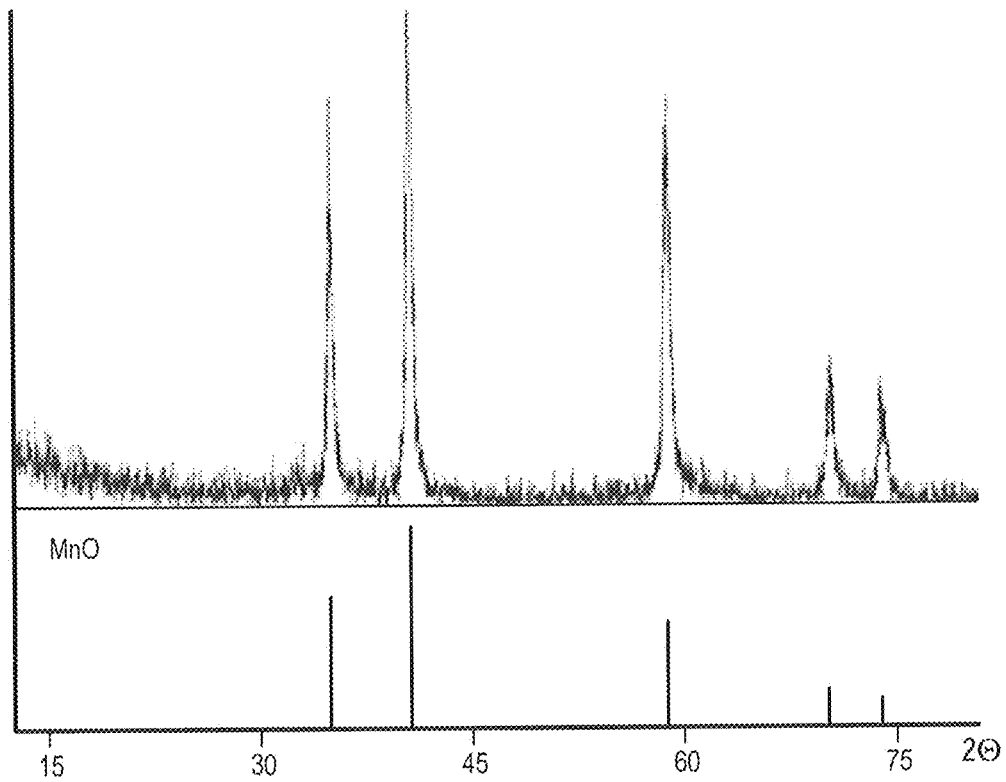
FIG. 3 is an X-ray diffraction (XRD) pattern of octahedral MnO nanoparticles as synthesized.

Example 1: Preparation of Manganese (II) Oxide Nanoparticles with Various Shapes <1-1> Preparation of Octahedral Manganese Oxide Nanoparticles The octahedral manganese (II) oxide nanoparticles were synthesized by using the method reported (Chem. Mater. 18: 1821, 2006) with some modifications. Briefly, manganese (II) formate ($Mn(HCOO)_2$, 5 mmol), oleic acid (13 mmol) and trioctylamine (15 mmol) were mixed in a 50 ml round-bottom flask. The mixture was heated in an oil bath to 120° C. with a magnetic stirring and kept at that temperature for 3 hours under a strong flow of argon gas. Then the temperature was increased to 330° C. with the heating rate of 30° C. per minute and the reaction was kept at that temperature until the green color appeared. The green solids were obtained by cooling the reaction solution down to room temperature and were washed with 1-propanol followed by a centrifugation (3 min, 3,500 rpm). The collected solids were washed again with ethyl alcohol several times before drying overnight in an oven. The results of TEM and XRD analysis are presented in FIG. 2 and FIG. 3, respectively.

<1-2> Preparation of Cross-Shaped Manganese Oxide Nanoparticles

Figure 4:
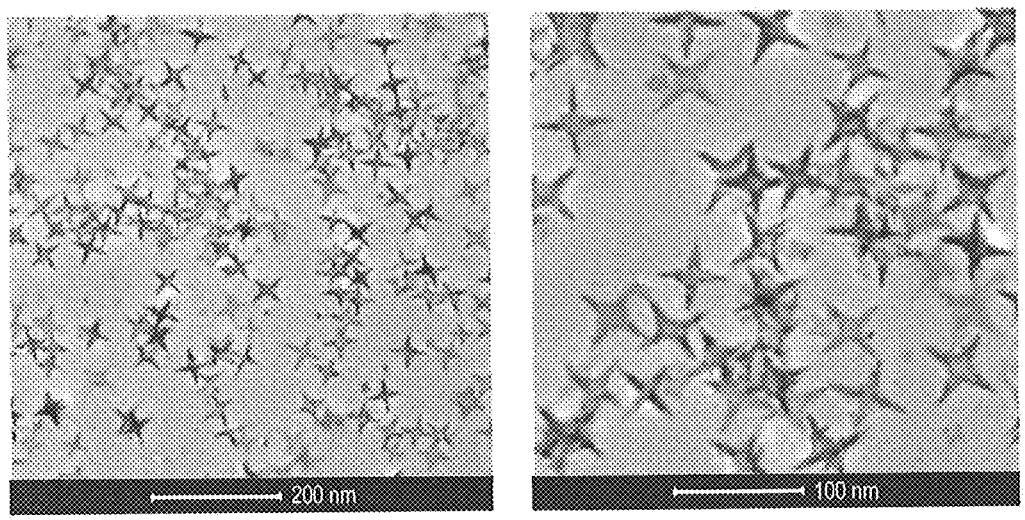
FIG. 4 is a TEM image of cross-shaped MnO nanoparticles.

Manganese (II) acetate (1.4 mmol), oleylamine (3.0 mmol), oleic acid (1.5 mmol) and trioctylamine (6.2 ml) were loaded into a 100 ml Schlenk tube. The Schlenk tube was heated in an oil bath to 270° C. with a heating rate of 18° C. per minute and kept at that temperature for 1 hour with magnetic stirring and argon gas flow. Then oleic acid (2.4 mmol) and trioctylamine (1.24 ml) were injected to the reaction mixture followed by further heating at the temperature of 270° C. for 1 h. The green solids were obtained by cooling the reaction solution down to room temperature and washed with 1-propanol followed by a centrifugation (3 min, 3,500 rpm). The collected solids were washed again with ethyl alcohol several times before drying overnight in an oven. The result of TEM analysis is presented in FIG. 4.

Figure 5:
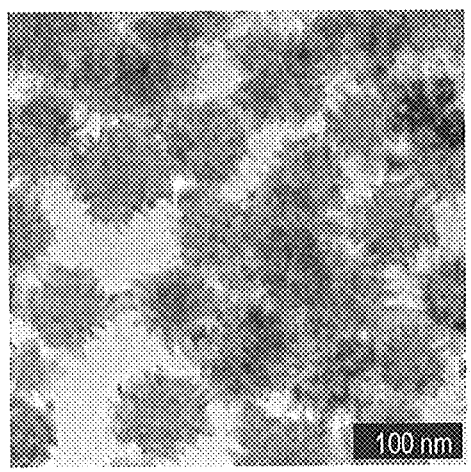
FIG. 5 is a TEM image of urchin-shaped MnO nanoparticles.

<1-3> Preparation of Urchin-Shaped Manganese Oxide Nanoparticles 6.2 ml trioctylamine, 1.4 mmol manganese (II) acetate, 3 mmol oleylamine and 1.5 mmol oleic acid were added to 100 ml Schlenk tube. The Schlenk tube was heated to 270° C. at a rate of 18° C./min in an oil bath under nitrogen blanket (the $N_2$ gas was blown at the flow rate of 40 cc/min). After 1 h at 270° C., the formation of large MnO nanoparticles was completed. Then the formed large polycrystalline MnO nanoparticles were subjected to facet-selective etching. Specifically, in order to affect the anisotropic etching, oleic acid (1.6 mmol) and trioctylamine (1.24 ml) was injected to the reaction mixture, and the resulting solution was further heated at 270° C. for 1 h. The reaction mixture was cooled to room temperature, and excess ethanol was added into the solution to give a brown precipitate. The result of TEM analysis is presented in FIG. 5.

<1-4> Preparation of Cubic Manganese Oxide Nanoparticles

Figure 6:
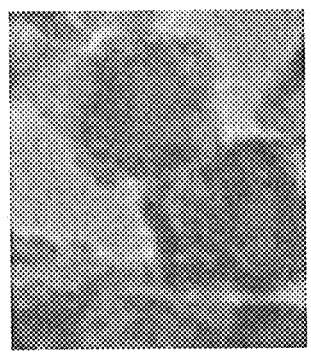
FIG. 6 is a TEM image of cubic MnO nanoparticles.

Manganese (II) acetate (0.4 mmol), sodium oleate (0.4 mmol) oleylamine (3.0 mmol), oleic acid (1.5 mmol) and trioctylamine (6.2 ml) were loaded into a 100 ml Schlenk tube. The Schlenk tube was heated in an oil bath to 270° C. with a heating rate of 18° C. per minute and kept at that temperature for 3 hour with magnetic stirring and argon gas flow. Then oleic acid (2.4 mmol) and trioctylamine (1.24 ml) were injected to the reaction mixture followed by further heating at the temperature of 270° C. for 1 h. The green solids were obtained by cooling the reaction solution down to room temperature and were washed with 1-propanol followed by a centrifugation (3 min, 3,500 rpm). The collected solids were washed again with ethyl alcohol several times before drying overnight in an oven. The result of TEM analysis is presented in FIG. 6.

Example 2: Preparation of Iron Oxide Nanoparticles with a Central MnO Phase

Figure 7:
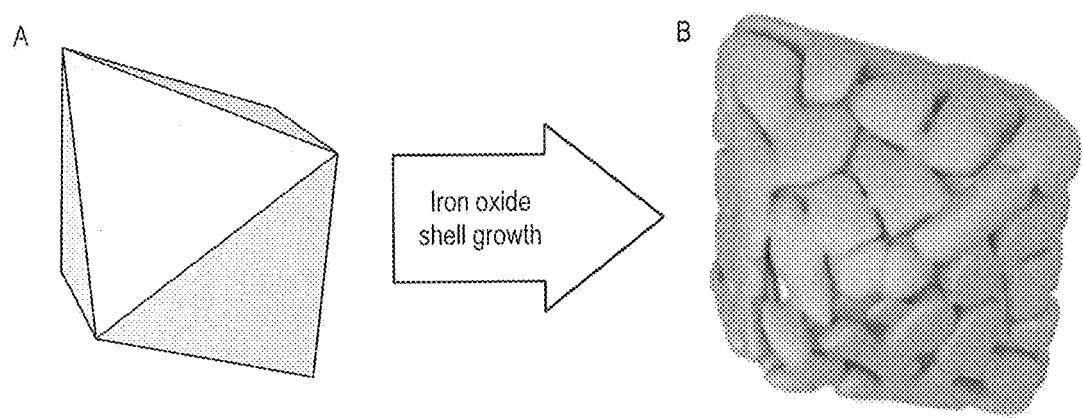
FIG. 7 is a diagram illustrating the synthesis scheme of nanoparticles of the present invention. (a) MnO nanoparticle and (b) iron oxide nanoparticle with a central MnO phase.
Figure 8:
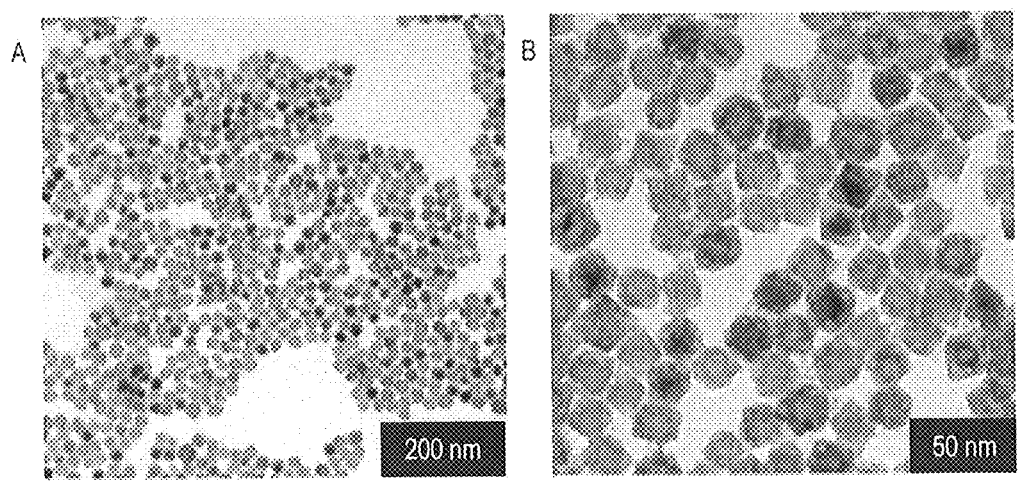
FIG. 8 is a TEM image of the iron oxide nanoparticle with a central MnO phase derived from octahedral MnO nanoparticles according to the present invention. (a) Low magnification, and (b) high magnification.
Figure 9:
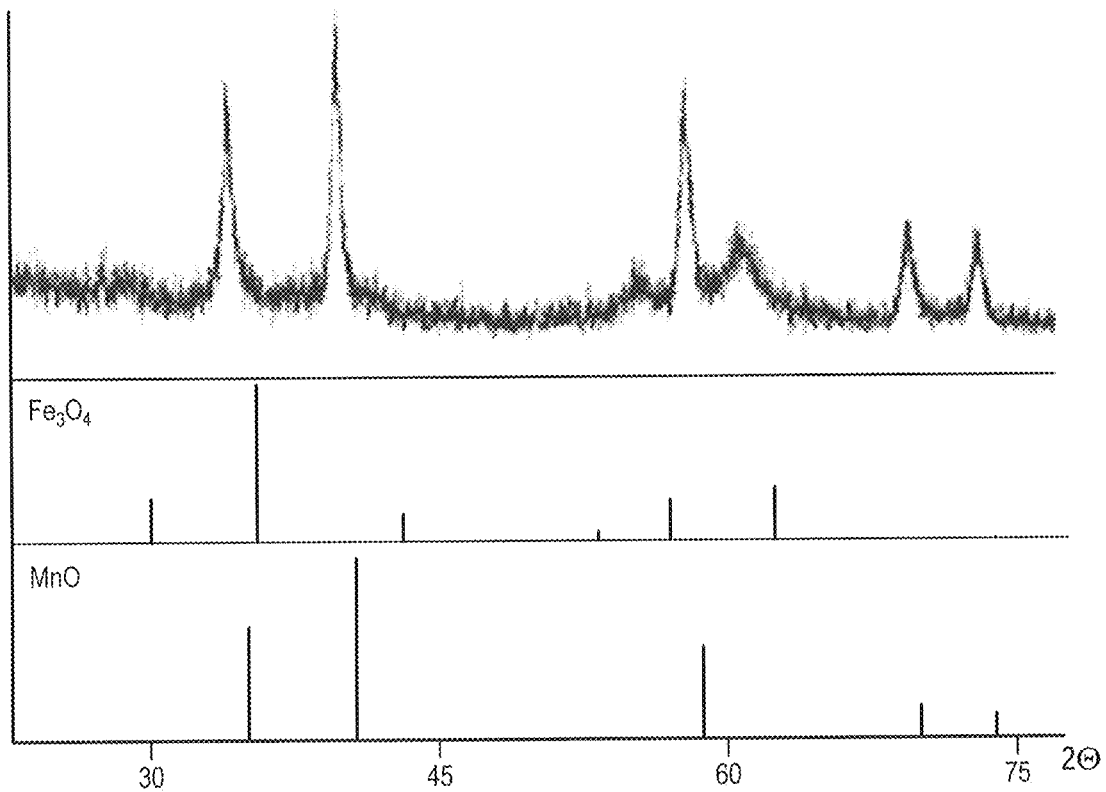
FIG. 9 is an XRD pattern of the iron oxide nanoparticle with a central MnO phase derived from octahedral MnO nanoparticles according to the present invention.
Figure 10:
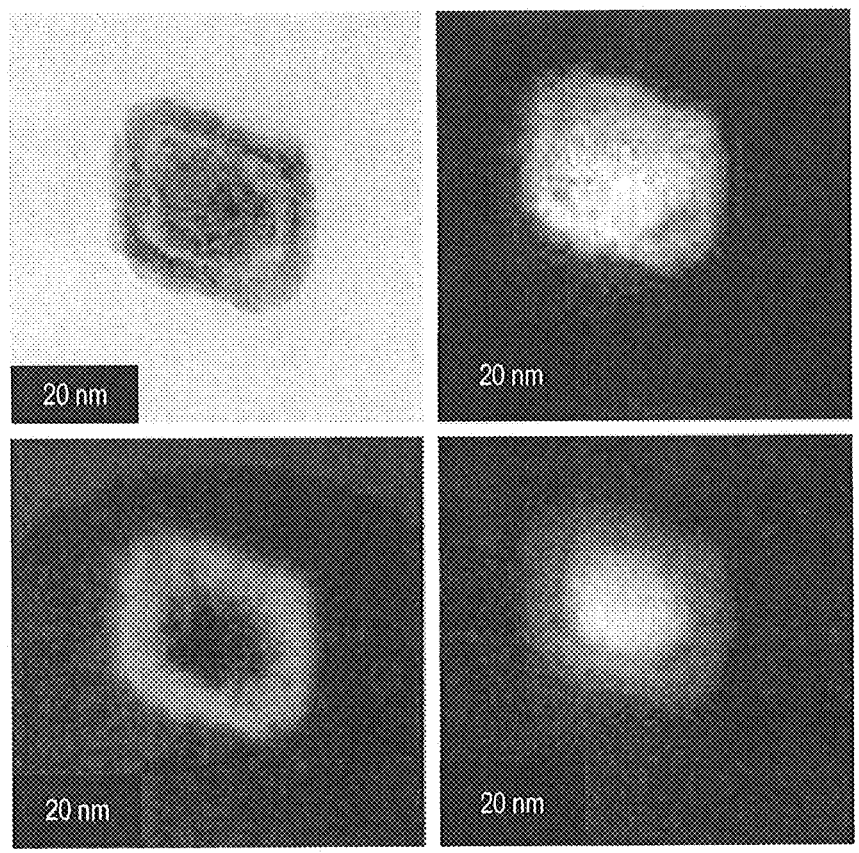
FIG. 10 is a result of electron energy loss spectroscopy (EELS) analysis of the iron oxide nanoparticle with a central MnO phase derived from octahedral MnO nanoparticles according to the present invention, showing the elemental mapping images for oxygen (white), iron (red) and manganese (green).

<2-1> Preparation of Iron Oxide Nanoparticles with a Central MnO Core Using Octahedral Manganese Oxide Nanoparticles 14.2 mg of the octahedral MnO nanoparticles and 0.375 mmol of iron (III) acetylacetonate were added into the solution of oleic acid (0.05 mmol), oleylamine (1 mmol) and trioctylamine (2 ml) in a 100 ml Schlenk tube. The Schlenk tube was heated in the oil bath to 210° C. with the heating rate of 10° C. per min under vigorous stirring and kept at this temperature for 20 min under argon. Then the reaction mixture was heated at 310° C. for 30 min under dry air environment (oxygen percentage is 20%). The black solution was cooled to room temperature. After cooling down to room temperature, the iron oxide nanoparticles with a central MnO phase core were precipitated with an addition of acetone and n-propanol and were collected by centrifugation (3 min, 3,500 rpm). The obtained nanoparticles were washed several times in hexane and ethanol. A diagram illustrating the synthesis scheme of the iron oxide nanoparticles with a central MnO core is presented in FIG. 7. The results of TEM and XRD analysis of the iron oxide nanoparticles with a central MnO core are presented in FIG. 8 and FIG. 9, respectively. The result of electron energy loss spectroscopy (EELS) analysis of the iron oxide nanoparticles with a central MnO core is presented in FIG. 10.

The resultant nanoparticles could be re-dispersed in chloroform, hexane or toluene for further using.

<2-2> Preparation of Iron Oxide Nanoparticles with a Central MnO Core Using Various Manganese Oxide Nanoparticles To examine the applicability of the present invention, the preparation of iron oxide nanoparticles with a central MnO core using various manganese oxide nanoparticles was performed. In these experiments, iron oxide nanoparticles with a central MnO core were prepared by the same manner as performed to prepare iron oxide nanoparticles with a central MnO core using octahedral manganese oxide nanoparticles in the above, except cross-shaped, urchin-shaped or cubic MnO nanoparticles were used instead of octahedral manganese oxide nanoparticles.

Figure 11:
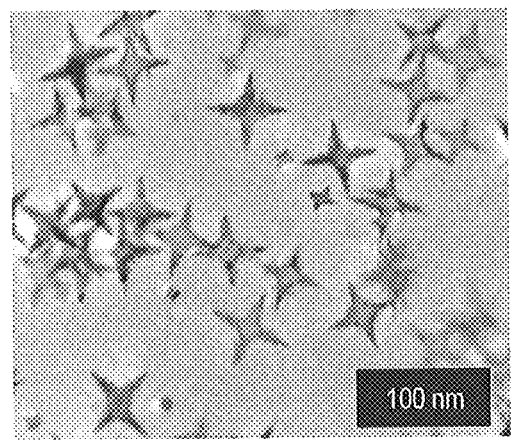
FIG. 11 is a TEM image of the iron oxide nanoparticle with a central MnO phase derived from cross-shaped MnO nanoparticles according to the present invention.
Figure 12:
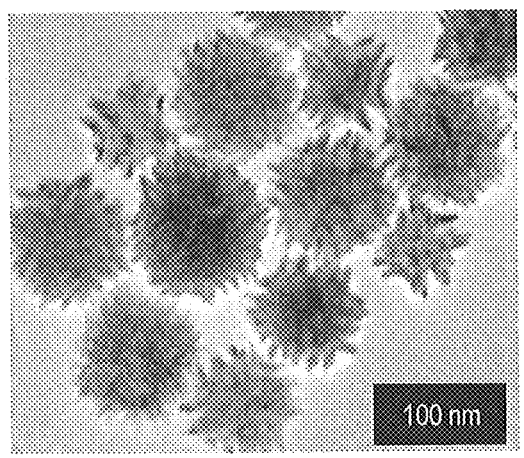
FIG. 12 is a TEM image of the iron oxide nanoparticle with a central MnO phase derived from urchin-shaped MnO nanoparticles according to the present invention.
Figure 13:
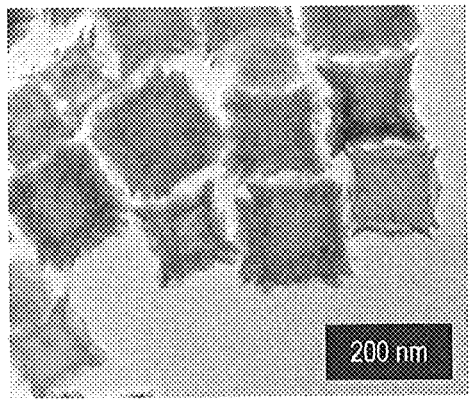
FIG. 13 is a TEM image of the iron oxide nanoparticle with a central MnO phase derived from cubic MnO nanoparticles according to the present invention.

The results of TEM analysis of the iron oxide nanoparticles with a central MnO core are presented in FIGS. 11-13.

The resultant nanoparticles could be re-dispersed in chloroform, hexane or toluene for further using.

Example 3: Preparation of Pyrenyl Polyethylene Glycol (Pyrenyl PEG)

Pyrenyl polyethylene glycol (pyrenyl PEG) was synthesized by conjugating the amino group of hetero-functional polyethylene glycol ($NH_2$—PEGCOOH, MW: 5,000 Da) with the n-hydroxysuccinimide (NHS) group of 1-pyrenebutyric acid n-hydroxysuccinimide ester (Py-NHS, Mw: 385.41 Da). In detail, 3 mmol of Py-NHS and 1 mmol of $NH_2$-PEG-COOH were dissolved in 15 ml of dimethyl formamide, and then 200 µl of triethylamine was added to the reaction mixture at room temperature. After reacting for 48 hours at room temperature under a nitrogen atmosphere, the resultant products were filtered and washed with excess ether. The precipitates were dried under a vacuum and stored for later use.

Example 4: Coating Iron Oxide Nanoparticles with Pyrenyl Polyethylene Glycol (Pyrenyl PEG)

The solution of iron oxide nanoparticles with a central MnO core in 1 ml of tetrahydrofuran (THF) was injected into 50 ml of phosphate buffer (pH 9.8) containing 300 mg of pyrenyl PEG. The resulting suspension was stirred overnight at room temperature to evaporate the organic solvent and subsequently centrifuged for 45 min at 20,000 rpm three times. After the supernatant was removed, the precipitates of iron oxide nanoparticles coated with pyrenyl PEG were re-dispersed in 10 ml of phosphate buffered saline (PBS; pH 7.4).

Example 5: Preparation of an MRI Contrast Agent Conjugated with Antibody

For efficient targeting, an MRI contrast agent prepared in Example 4 was conjugated with antibody. In detail, 10 µmol of 1-ethyl-3-(3-dimethylaminopropyl) carbodiimide (EDC) and 10 µmol of sulfo-n-hydroxysuccinimide (sulfo-NHS) as cross-linkers were added in 5 ml of the MRI contrast agent solution prepared in Example 4. And then, 0.7 mg (4.5 nmol) of anti HER2/neu antibody (Herceptin®; HER, Roche Pharmaceutical Ltd.) was added. The mixture was allowed to stand at 4° C. After 6 h, the MRI contrast agents conjugated with antibody (HER-conjugated MRI contrast agent) were purified by centrifugation (20,000 rpm, 45 min). Similarly, the irrelevant human immunoglobulin G (IgG) antibody (IRR) was conjugated with the MRI contrast agents by the same manner as performed to prepare the HER-conjugated MRI contrast agents in the above, except IRR was used instead of HER. The prepared IRR-conjugated MRI contrast agent was used as control MRI contrast agents without targeting molecule.

Example 6: T2-Weighted MR Imaging 0.5 ml of HER-conjugated MRI contrast agents were administered to nude mice. And then MR imaging was performed using a 3T clinical MRI instrument with a micro-47 surface coil (Philips Medical Systems, The Netherlands). The T2-weighted MR images of nude mice injected with HER-conjugated MRI contrast agents at 3T were acquired using the following measurements at room temperature: TR=4,000 milliseconds even echo space, number of acquisitions=1, point resolution of 312×312 µm, section thickness of 0.6 mm and TE=60 msec. The results are shown in FIG. 14.

Figure 14:
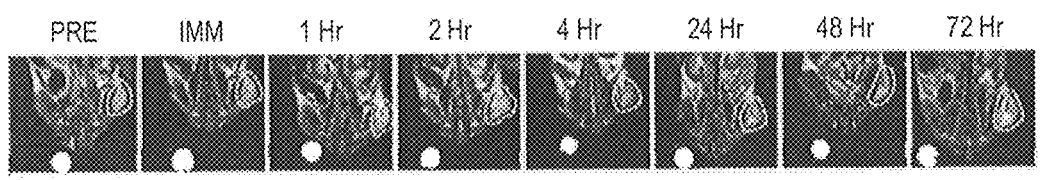
FIG. 14 is a T2-weighted MR image obtained using the MRI contrast agents of the present invention.

The result in FIG. 14 confirmed that the MRI contrast agent of the present invention could be used as an effective T2 MRI contrast agent.

Example 7: T1-Weighted MR Imaging 0.5 ml of HER-conjugated MRI contrast agents were administered to nude mice. And then MR imaging was performed using a 3T clinical MRI instrument with an 11×14 cm SENSE flex M coil having two elliptical elements (Philips Medical Systems, The Netherlands). The T1-weighted MR images of nude mice injected with HER-conjugated MRI contrast agents at 3T were acquired with selected echo time of 0.07 ms. The results are shown in FIG. 15.

Figure 15:
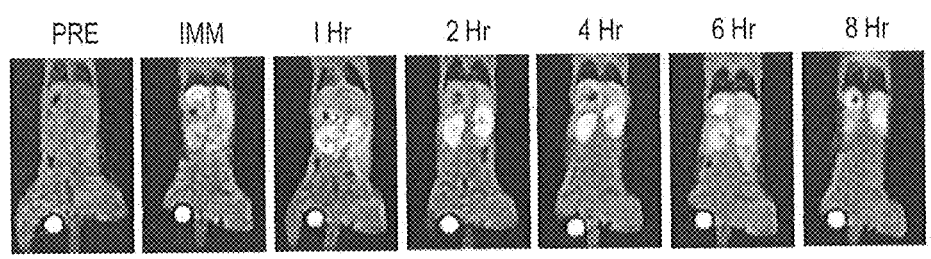
FIG. 15 is a T1-weighted MR image obtained using the MRI contrast agents of the present invention.

The result in FIG. 15 confirmed that the MRI contrast agent of the present invention could be used as an effective T1 MRI contrast agent.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for producing a T1-T2 dual-mode MRI contrast agent derived from nanoparticles that have a core of manganese oxide and a porous shell of manganese ion-doped iron oxide on the core, comprising the following steps:
   A) synthesizing manganese oxide nanoparticles under argon gas environment;
   B) forming an epitaxial layer of iron oxide on the surface of manganese oxide nanoparticles under argon gas environment;
   C) maintaining the formation of the layer of porous manganese ion-doped iron oxide under dry air environment to form multilayer nanoparticles having a porous shell adjacent to core structure; and
   D) coating multilayer nanoparticles with a pyrenyl polyethylene glycol,
   wherein the manganese oxide is octahedral shape or cross shape.

2. The method for producing a T1-T2 dual-mode MRI contrast agent according to claim 1, wherein the pyrenyl polyethylene glycol is modified by conjugation with targeting moieties or diagnostic moieties.

3. The method for producing a T1-T2 dual-mode MRI contrast agent according to claim 2, wherein the targeting moiety is selected from the group consisting of antibodies, antibody fragments, aptamers, and various ligands binding to receptors displayed on the surface of target cell.

4. The method for producing a T1-T2 dual-mode MRI contrast agent according to claim 2, wherein the diagnostic moiety is selected from the group consisting of fluorophores, optical reporters, quantum dots, computed tomography probes and nonmetallic radioisotopes.

* * * * *